(12) United States Patent
Morgan

(10) Patent No.: US 12,171,679 B2
(45) Date of Patent: Dec. 24, 2024

(54) STENT HAVING REDUCED AXIAL SHRINKAGE UPON RADIAL EXPANSION

(71) Applicant: NuMED, Inc., Hopkinton, NY (US)

(72) Inventor: Gareth J. Morgan, Denver, CO (US)

(73) Assignee: NuMed, Inc., Hopkinton, NY (US)

( * ) Notice: Subject to any disclaimer, the term of this patent is extended or adjusted under 35 U.S.C. 154(b) by 228 days.

(21) Appl. No.: 17/320,682

(22) Filed: May 14, 2021

(65) Prior Publication Data
US 2022/0362043 A1 Nov. 17, 2022

(51) Int. Cl.
*A61F 2/958* (2013.01)
*A61F 2/95* (2013.01)

(52) U.S. Cl.
CPC ............ *A61F 2/958* (2013.01); *A61F 2/9526* (2020.05); *A61F 2210/0014* (2013.01)

(58) Field of Classification Search
CPC .... A61F 2002/91575; A61F 2002/9155; A61F 2002/91558; A61F 2/915; A61F 2002/91508; A61F 2002/91516; A61F 2002/91525
See application file for complete search history.

(56) References Cited

U.S. PATENT DOCUMENTS

| | | | |
|---|---|---|---|
| 4,733,665 A | 3/1988 | Palmaz | |
| 5,868,783 A | 2/1999 | Tower | |
| 6,022,370 A | 2/2000 | Tower | |
| 2003/0033003 A1* | 2/2003 | Harrison | A61F 2/915 623/1.15 |
| 2003/0199971 A1 | 10/2003 | Tower et al. | |
| 2004/0073290 A1* | 4/2004 | Chouinard | A61F 2/91 623/1.15 |
| 2004/0215323 A1* | 10/2004 | Stiger | A61B 17/00234 623/1.15 |
| 2008/0221664 A1* | 9/2008 | Bales | A61F 2/88 623/1.22 |

* cited by examiner

*Primary Examiner* — Thomas McEvoy
(74) *Attorney, Agent, or Firm* — Barclay Damon LLP

(57) ABSTRACT

An intraluminal stent includes pluralities of first and second wire segments made from a soft malleable alloy formed into a cylindrical structure. Each of the wire segments is defined by a series of sinusoidal bends formed over the length of each segment, with the initial unformed length of each second wire segment being larger than that of each first wire segment. Each of the first and second wire segments include the same number of sinusoidal bends with the amplitude of the of the sinusoidal bends of the second wire segments being larger than that of the sinusoidal bends of the first wire segments. Adjacent wire segments are conjoined by welds at apices of each sinusoidal bend to form the cylindrical or tubular structure. The first wire segments can form a center portion of the stent and the second wire segments can be provided at either or both ends of the stent, enabling minimized axial shrinkage when the stent is radially expanded from an initial to an expanded diameter and in which the second wire segment at the terminal end of the stent is caused to outwardly flare significantly relative to the remainder of a radially expanded stent.

12 Claims, 6 Drawing Sheets

STENT HAVING REDUCED AXIAL SHRINKAGE UPON RADIAL EXPANSION

TECHNICAL FIELD

This application is generally directed to the field of medical stents and more specifically to an implantable intravascular stent that can be radially expanded, such as by means of balloon catheterization. The herein described stent exhibits limited axial shrinkage following radial expansion from an initial to an expanded diameter.

BACKGROUND

The basic concept of radially expandable intravascular stents is well known in the medical field. More specifically, a cylindrically shaped sleeve having a first diameter is placed over a collapsed balloon catheter and then inserted into an occluded blood vessel of a subject. Upon inflation of the balloon to a specific pressure, the stent is permanently deformed to a larger second diameter and into contact and support with the interior walls of the blood vessel. After subsequent deflation of the balloon and removal of the catheter, the implanted stent remains supported to the interior wall of the blood vessel at the radially expanded second diameter.

One form of expandable stent is described in U.S. Pat. No. 4,733,665 to Palmaz et al. The Palmaz stent is defined by plurality of interconnected elongate elements made from a material, such as stainless steel or tantalum. The elongate segments are arranged and welded in a criss-cross arrangement in order to form a unitary cylindrical structure. The Palmaz stent can be positioned on an collapsed balloon for implantation in a blood vessel of interest. However, the stent is designed to be expanded only a single time and only to a single diameter.

More recently, Applicant has designed a deformable stent, as described in U.S. Pat. No. 6,022,370, herein incorporated by reference in its entirety, in which a series of fine wire segments are each bent into a serpentine ribbon. The wire segments are then wound around a cylindrical mandrel to form a cylindrical sleeve for application onto a collapsed balloon catheter for transluminal insertion in a blood vessel and later expansion of the balloon catheter at the desired site. Each of the fine wire segments of the stent are formed from a malleable shape memory metal material, such as nitinol that has sufficient strength, but which also advantageously enables plastic expansion that is maintained following expansion. Moreover, the stent can be additionally expanded, if needed, and also can be locally deformed such that the stent can assume more than one expanded diameter. Stents, such as those described above can be additionally covered, for example, using a sleeve of ePTFE or other suitable biologically suitable material.

One issue in the use any radially expandable intravascular stents is that of axial shrinkage of the stent following radial expansion by the inflated balloon, which is not desirable. It is therefore a general need in the field to minimize the amount of axial shrinkage of an intravascular stent during radial expansion as much as possible. It is a further prevailing need in the field to insure the stent remains in place and to minimize stent migration as much as possible.

BRIEF DESCRIPTION

Therefore and according to an aspect, there is provided an intraluminal stent comprising a first end and a second end, the stent made from a malleable material. The stent comprises a plurality of first wire segments having an initial or unformed length and a plurality of second wire segments having an initial or unformed length that is longer than the initial or unformed length of the first wire segments. Each of the first and second wire segments are formed with a series of sinusoidal bends in a serpentine pattern in which the length (amplitude) of each of the sinusoidal bends formed in each second wire segments is larger than the length of each of the sinusoidal bends formed in each first wire segment. Each of the first and second wire segments are wound onto a mandrel to define a cylindrical structure with adjacent wire segments being welded to one another at respective apices of the sinusoidal bends and with the second wire segments being at disposed either the first end, the second end or at both ends of the stent.

The first and second wire segments are preferably made from a highly malleable material, such as an alloy of platinum and iridium that has been fully annealed to remove as much spring memory as possible. A preferred material is an alloy made up of 90 percent platinum and 10 percent iridium. Other suitable metal alloys, such as nitinol and cobalt chromium, can also be used.

In one version, at least two of the second wire segments are attached to only one of the first and second ends of the stent and in another version at least two of the second wire segments are disposed at both ends of the stent. The terminal end of the stent having the at least two wire segments is configured to outwardly flare relative to a diameter of the remainder of the stent upon radial expansion.

In at least one other embodiment, a third wire segment is disposed at the terminal end of the stent. The third wire segment has an initial or unformed length that is shorter than the initial or unformed length of the second wire segments. The third wire segment further has a series of sinusoidal bends formed in a serpentine pattern in which respective apices of the sinusoidal bends are welded to an adjacent second wire segment.

The initial length and the amplitude of the sinusoidal bends formed in the third wire segment according to at least one embodiment is substantially equal to the initial length and amplitude of the sinusoidal bends formed in each of the first wire segments.

According to yet another aspect, there is provided a stent implantation system comprising a balloon catheter and a stent, the stent having a cylindrical configuration and made from a malleable material, the stent having a first diameter and a second diameter that is larger than the first diameter when the stent is expanded radially. The stent comprises a plurality of first wire segments having a first unformed or initial length and a plurality of second wire segments having a second initial or unformed length that is longer than the first length. Each of the first and second wire segments are formed into a serpentine pattern including a plurality of sinusoidal bends in which the length (amplitude) of each of the sinusoidal bends formed in the second wire segments is larger than the length of each of the sinusoidal bends formed in the first wire segments. Each of the first and second wire segments are wound onto a mandrel to define a cylindrical structure in which adjacent wire segments are welded to one another at respective apices of the sinusoidal bends. The second wire segments having the longer sinusoidal bends is disposed at either the first end, the second end or at both ends of the stent.

According to at least one embodiment, at least two second wire segments are attached to each of the first and second ends of the stent. In another version, the at least two second wire segments are attached to only one of the first or second ends of the stent such that least one terminal end of the stent having the at least two second wire segments is configured to flare significantly outward upon radial expansion as compared to the remainder of the stent.

In at least one version, the intravascular stent further comprises a third wire segment disposed at a terminal end of the stent. The third wire segment has an initial length and a series of formed sinusoidal bends wherein the initial length and amplitude of the formed sinusoidal bends of the third wire segment are shorter than the initial length and the amplitude of the sinusoidal bends of the second wire segments.

According to yet another aspect, there is provided a method of manufacturing a stent having reduced axial shrinkage, the method comprising the steps of providing a plurality of first wire segments and a plurality of second wire segments, the first wire segments having a first initial or unformed length and the second wire segments having a second initial or unformed length that is longer than the first length. The first and second wire segments are formed into a serpentine pattern made up of a number of sinusoidal bends with each of the first and second wire segments having the same number of sinusoidal bends. Each of the first and second wire segments are wound about a mandrel to form a cylindrical structure in which adjacent wire segments are welded to one another at adjacent apices of the formed sinusoidal bends.

In at least one version, the first wire segments are disposed in a center portion of the stent and the second wire segments are disposed at opposing ends. According to at least one embodiment, at least two wire second segments are disposed at each end of the stent. In another embodiment, the second wire segments are disposed at only one end.

In at least one embodiment, the ends of the stent having the longer wire segments flare outwardly upon radial expansion, such as through inflation of a balloon on which the stent is disposed. In at least one embodiment, at least one wire segment having a third length, which is shorter than that of the length of the second wire segment(s), can be disposed at a terminal end of the stent. In one version, the length of the at least one third wire segment is substantially equal to that of the length of the first plurality of wire segments.

One advantage realized by the present invention is that the herein described stent exhibits considerably less axial shrinkage following radially expansion, such as via a balloon catheter onto which the stent is disposed. Accordingly, more effective retention is achieved within a working lumen of a subject due to the increased working length of the stent.

In addition and by providing at least one end portion having the longer sinusoidal bends, flaring can be achieved. This flaring effect which improves stent retention and also minimizes migration. In addition, the flaring of the stent also reduces the potential risk of coronary or pulmonary vein compression in adjacent blood vessels to the vessel being stented.

Additionally, the herein described stent can be manufactured using existing tooling fixtures used in the manufacture of other known and radially expandable stents.

These and other features and advantages will be readily understood from the following Detailed Description, which should be read in conjunction with the accompanying figures.

DETAILED DESCRIPTION

The following description relates to embodiments of an intravascular stent configured to exhibit reduced axial shrinkage following radial expansion, as compared to other radially expandable prior art stents used for implantation within a body lumen of a patient. It will be readily apparent to one of sufficient skill that there are a number of modifications and variations that can be made to the herein described design that are within the intended scope of this invention. In addition, certain features are described in conjunction with the accompanying drawings to provide an adequate frame of reference. These terms, which include "distal", "proximal", "inner", "outer", "above" and "below", among others should not be relied upon as limiting to the intended scope of the invention, unless so specifically indicated herein. Still further, the figures depicted in this application are not necessarily intended to be to scale and therefore should not be relied upon for scaling purposes.

Figure 1:
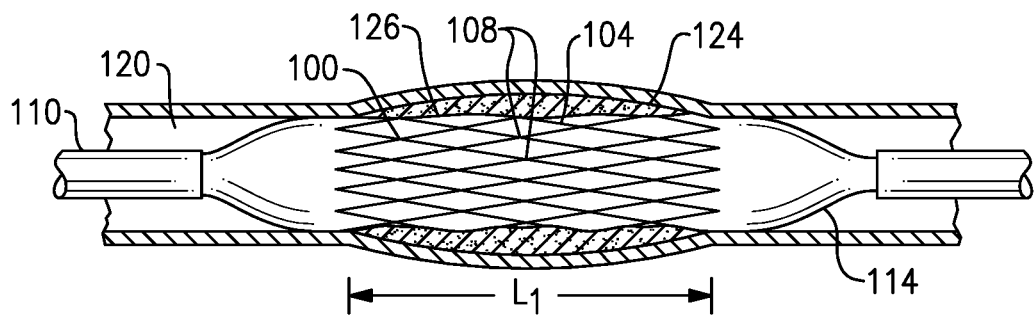
FIG. 1 is a side elevational view of a known intraluminal stent, which is shown in an initial unexpanded condition.
Figure 2:
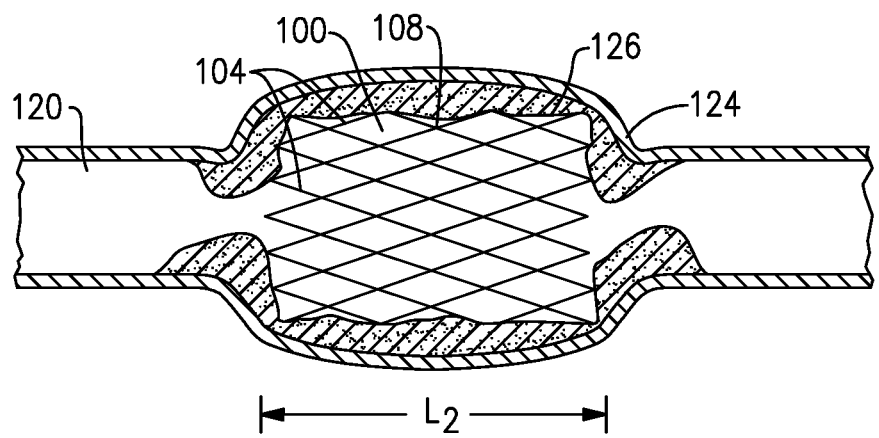
FIG. 2 is the side elevational view of the known intraluminal stent of FIG. 1, which is shown in a radially expanded condition.

FIGS. 1 and 2 illustrate a first known radially expandable prior art stent 100, and more specifically a stent as described by U.S. Pat. No. 4,733,665 issued to Palmaz, which is placed over a collapsed balloon 114 of a balloon catheter 110 and positioned within a blood vessel 120 of interest having an occluded portion 124. The collapsed balloon 114 is then inflated to allow the stent 100 to controllably assume a second radial diameter, shown in FIG. 2, in contact with the interior wall 126 of the blood vessel 120. The herein described stent 100 is formed of a series of interconnected criss-crossing elongate members 104, each made from stainless steel or tantalum, in which the elongate members 104 are welded at intersecting points 108 in order to define a unitary cylindrical structure that expands uniformly upon inflation. As is apparent from FIGS. 1 and 2, a radial expansion of the stent 100 causes a corresponding decrease in axial length, shown figuratively as the difference between $L_1$ and $L_2$, whereby the herein-described stent 100 could lose 40-50 percent or more in length due to axial shrinkage following inflation.

Figure 4:
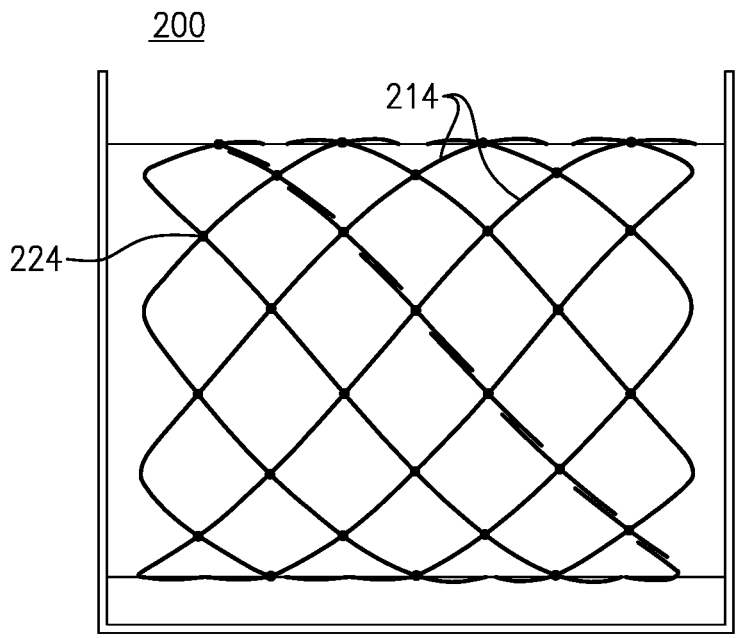
FIG. 4 is the side elevational view of the known intraluminal stent of FIG. 3, as shown in a radially expanded condition.
Figure 3:
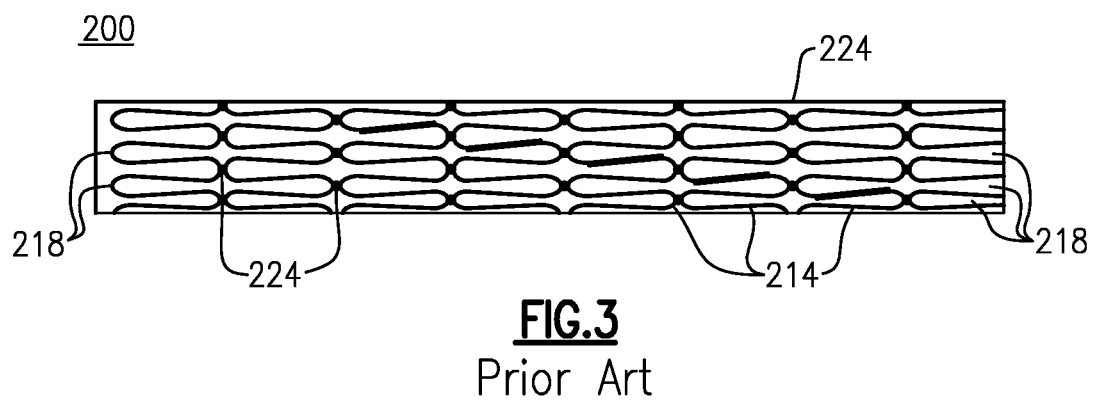
FIG. 3 is a side elevational view of another known intraluminal stent, which is shown in an initial unexpanded condition.

With reference to FIGS. 3 and 4, another known intraluminal stent 200 is described that is made in accordance with aspects of U.S. Pat. No. 6,022,370 and U.S. Patent Application Publication No. 2003/0199971 A1, each of which are incorporated by reference in their entirety. The intraluminal stent 200 is defined by a series of fine wire ribbons or strands, each designated 214 that are joined together to create a tubular or cylindrical member. The wire strand of each section 214 is fabricated from a soft, highly malleable metal alloy that has been fully annealed to remove as much of its shape memory as possible. Preferably, the wire material is fabricated of an alloy consisting of about 90 percent platinum and 10 percent iridium and having a tensile strength of between 150,000 psi and 175,000 psi.

In terms of manufacture, the plurality of wire ribbons or strands 214 are identical in terms of their length and diameter. More specifically and prior to winding the wire ribbons 214 into a cylindrical shape, each wire ribbon 214 is formed so that it includes a plurality of sinusoidal bends 218. The sinusoidal bends 218 can be formed by winding each wire strand(s) 214 between rows of vertical pins (not shown) projecting from the surface of a flat substrate (not shown). Each wire strand 214 is wound about the vertical pins in alternate rows to create sinusoidal shaped ribbon sections having a desired number of bends 218, with each wire segment 214 having the same number of sinusoidal bends 218. Each of the sinusoidal bends 218 include an apex and an open end, which alternate along a serpentine pattern.

Each wire ribbon section 214 is then wound onto a cylindrical mandrel (not shown) with each wire ribbon 214 being placed in axial alignment such that the apex of each sinusoidal bend 218 is located in close proximity with the apex of a sinusoidal bend 218 on an adjacent ribbon 214. The adjacent bends 218 are then welded together, as designated at 224, in order to conjoin the wire ribbons 214 in assembly. Free ends of each of the wire ribbons 214 can also be bent into parallel overlapping alignment and can be conjoined using similar section welds.

The formed stent 200 is removed from the mandrel (not shown) and is sized for disposition onto an inflatable balloon such as that partially shown in FIGS. 1 and 2 of a balloon catheter 110, which includes at least one expandable balloon 114. The defined cylindrical structure of the stent 200 which is made from the highly malleable and annealed material permits local expansion based on the amount of radial pressure applied to the stent 200 during inflation of the balloon 114 following implantation of the stent 200 into a body lumen of a patient during a surgical procedure. Further details relating to the manufacture of the known stent are provided in U.S. Pat. No. 6,022,370 and U.S. Patent Application Publication No. 2003/0199971 A1, each previously incorporated in their entirety.

Figure 6:
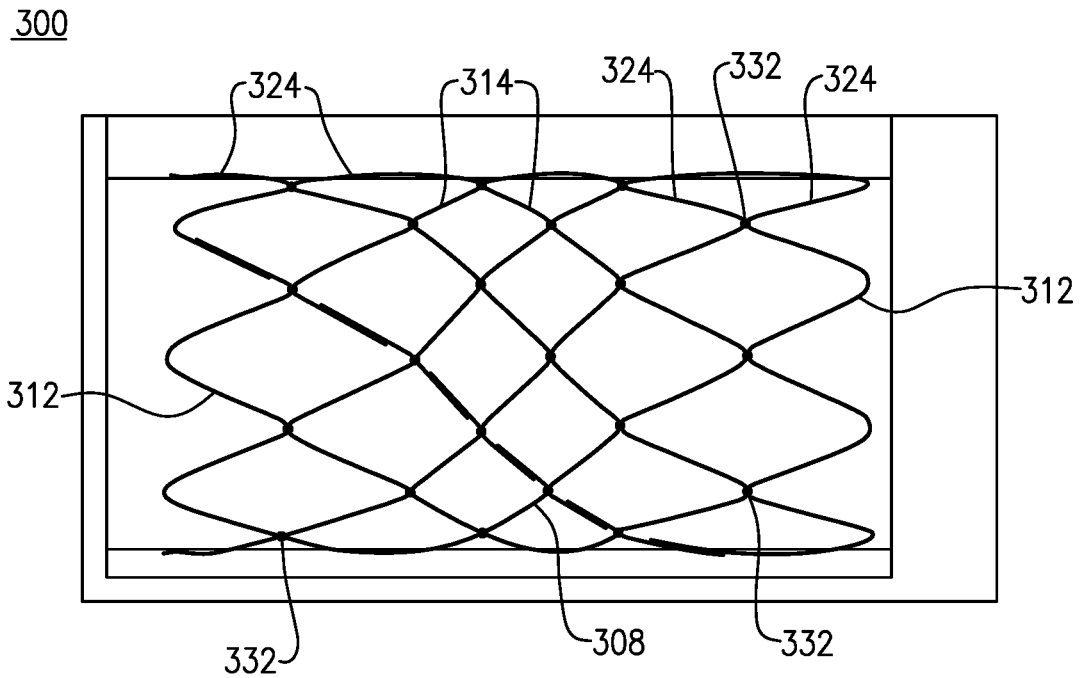
FIG. 6 is a side elevational view of the intraluminal stent of FIG. 5, shown in a radially expanded condition.
Figure 5:
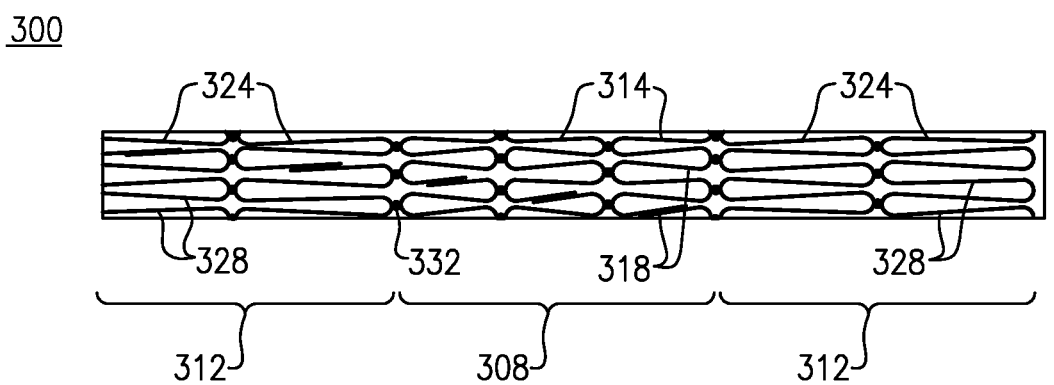
FIG. 5 is a side elevational view of an intraluminal stent made in accordance with an exemplary embodiment and shown in an initial unexpanded condition.

With reference to FIGS. 5-6, there is described a radially expandable stent 300 made in accordance with an exemplary embodiment. The stent 300 according to this embodiment includes a center portion 308 and a pair of opposing end portions 312. The center portion 308 is defined by a plurality of a plurality of first wire segments 314, while the end portions 312 are each defined by a plurality of second wire segments 324. Each of the first and second wire segments 314, 324 are made from a soft and highly malleable material like that of the previously described stent 200 that has been highly annealed to remove as much shape memory as possible. According to this specific embodiment, the wire segments 314, 324 are fabricated from an alloy that is approximately 90 percent platinum and approximately 10 percent iridium, the wire segments 314, 324 having a diameter of approximately 0.33 mm. Other suitable materials, such as cobalt chromium or nitinol can also be used.

Each of the first wire segments 314 are defined by a first length and formed with a first series of sinusoidal bends 318 in a serpentine pattern. The sinusoidal bends 318 can be formed by winding each strand of wire 314 between rows of vertical pins (not shown) projecting from the surface of a flat substrate (not shown). Each wire strand 314 is wound about the vertical pins in alternate rows to create sinusoidal shaped sections having a desired number of sinusoidal bends 318 Each sinusoidal bend 318 is substantially defined by a tear drop-shape defined by an apex and an open end, wherein the series of sinusoidal bends 318 are defined by alternating apices and open ends in the formed serpentine pattern.

Prior to forming, each of the second wire segments 324 are defined by an overall initial length that is longer than the unformed or initial length of each of the first wire segments 314. As noted, the second wire segments 324 are also formed with a corresponding second series of sinusoidal bends 328 in a similar manner with the first and second wire segments 314, 324 each having the same number (frequency) of formed sinusoidal bends 318, 328. Accordingly, the axial distance between alternating apices of each of the second sinusoidal bends 328 is longer than that of the first series of sinusoidal bends 318. For clarity and put another way, the first and second wire segments 314, 324 are formed with sinusoidal bends 318, 328 having the same frequency, but in which the amplitude of the second series of sinusoidal bends 328 is larger than that of the first series of sinusoidal bends 318. According to this specific embodiment, each of the first and second wire segments 314, 324 preferably include a total of 8 or 10 sinusoidal bends 318, 328 over its length, although this parameter can be suitably varied with the formed lengths of the first and second plurality of wire segments being equal due to the formation of different sized sinusoidal bends.

Each formed wire segment 314, 324 is then wound onto a cylindrical mandrel (not shown). According to this specific embodiment, a total of three (3) wire segments 314 form the center portion 308 of the stent 300, while two pairs of the second wire segments 324 form the respective opposing end portions 312 of the stent 300. It will be understood that the number of first and second wire segments 314, 324 can be suitably varied, depending on the desired initial axial length of the stent 300.

The wire segments 314, 324 are placed in axial alignment such that the apex of each sinusoidal bend 318, 328 is located in close proximity with the apex of a sinusoidal bend 318, 328 on an adjacent wire segment 314, 318. The adjacent bends 318, 328 are then welded together, as designated at 332, at the respective apices in order to conjoin the wire segments 314, 324 in assembly. Suitable welding can be performed by means of laser welding or through use of gold-base brazing alloys, among others.

The herein described stent 300 can be disposed and suitably crimped onto a collapsed balloon 110 of a balloon catheter 110, such as the catheter partially shown in FIGS. 1 and 2 as part of a stent implantation system. The catheter balloon 114 is preferably made from a nylon or other flexibly expandable material and crimped thereon. The stent 300 is placed on the uninflated balloon 114 with sufficient adherence to prevent shifting during positioning in the blood vessel 120, FIG. 1. The catheter 110 is then guided into the desired location in a blood vessel by means of an introducer (not shown) using a guide wire (not shown) in a manner known to those in the field.

The stent 300 being fabricated from a highly malleable material, can assume a crimped position on the collapsed balloon catheter 110 without sacrificing its intended function and with minimum risk of puncturing the balloon. Once the stent 300 is properly located and the location is verified by fluoroscopic inspection or other means, the collapsed balloon 114 of the catheter 110 is then inflated in a manner that is well known and the stent 300 is radially expanded in conformity with the expansion of the balloon profile due to the malleability of the stent material.

To demonstrate the advantages of the present invention, a plurality of stents 300, FIGS. 5 and 6, made in accordance with the herein described design were fabricated and bench-tested alongside a corresponding plurality of the prior design stents 200, FIGS. 3 and 4. More specifically, the stents 200, 300 were bench tested on an inflatable balloon and inflated from an initial diameter to a series of inflated diameters with an initially measured axial length being compared to a measured axial length following each radial expansion.

As further represented by the following Table 1, the overall amount of axial shrinkage ($L_0$–$L_1$) exhibited by each stent 200, 300 was determined following radial expansion by the balloon catheter or other suitable inflation or expansion means onto which each stent 200, 300 was disposed, permitting radial expansion of each stent 200, 300 to its expanded diameter. For purposes of the comparison, four (4) families of stents 200, 300 were tested having 8 sinusoidal bends and inflatable diameters between 12 mm and 24 mm and four (4) additional families of stents 200, 300 were tested having 10 sinusoidal bends and inflatable diameters between 26 mm and 30 mm. The results of this comparison are tabulated, as follows:

TABLE 1

| Diameter | Prior Stent | | New Stent | |
|---|---|---|---|---|
| | Length | % Shrinkage | Length | % Shrinkage |
| 8Z45 | | | | |
| Initial | 43.38 | | 45.98 | |
| 12 mm | 41.7 | 3.8 | 44.39 | 3.45 |
| 14 mm | 39.7 | 8.4 | 43.82 | 4.71 |
| 15 mm | 39.4 | 9.2 | 43.35 | 5.71 |
| 16 mm | 38.4 | 11.4 | 42.83 | 6.84 |
| 18 mm | 37.1 | 14.5 | 41.97 | 8.64 |
| 20 mm | 32.7 | 24.7 | 40.6 | 11.71 |
| 22 mm | 31.5 | 27.3 | 39.4 | 14.3 |
| 24 mm | 28.3 | 34.9 | 37.97 | 17.43 |
| 8Z50 | | | | |
| Initial | 50.03 | | 51.51 | |
| 12 mm | 47.06 | 6.17 | 49.79 | 3.79 |
| 14 mm | 45.81 | 8.67 | 49.06 | 5.16 |
| 15 mm | 44.99 | 10.30 | 48.46 | 6.09 |
| 16 mm | 44.21 | 11.87 | 48.01 | 7.18 |
| 18 mm | 42.07 | 16.14 | 46.58 | 9.44 |
| 20 mm | 39.64 | 20.97 | 45.37 | 11.96 |
| 22 mm | 37.11 | 26.01 | 43.69 | 15.15 |
| 24 mm | 33.34 | 33.53 | 41.45 | 19.47 |
| 8Z55 | | | | |
| Initial | 54 | | 57 | |
| 12 mm | 52.5 | 5.00 | 55.12 | 3.31 |
| 14 mm | 51.1 | 7.60 | 54.16 | 4.98 |
| 15 mm | 49.8 | 10.00 | 53.65 | 5.88 |
| 16 mm | 49.1 | 11.2 | 53.07 | 6.91 |
| 18 mm | 47 | 15.10 | 51.73 | 9.25 |
| 20 mm | 43.3 | 20.00 | 49.91 | 12.44 |
| 22 mm | 40.9 | 26.10 | 48.211 | 15.60 |
| 24 mm | 37.2 | 32.80 | 45.44 | 20.29 |
| 8Z60 | | | | |
| Initial | 60.7 | | 62.72 | |
| 12 mm | 58.4 | 4.50 | 60.37 | 3.76 |
| 14 mm | 56.7 | 7.30 | 59.45 | 5.23 |
| 15 mm | 55.5 | 9.20 | 58.87 | 6.18 |
| 16 mm | 54.3 | 11.20 | 58.08 | 7.41 |
| 18 mm | 52 | 14.90 | 56.79 | 9.46 |
| 20 mm | 49.2 | 19.50 | 54.65 | 12.87 |
| 22 mm | 45.5 | 25.50 | 52.62 | 16.10 |
| 24 mm | 41.4 | 32.30 | 50.02 | 20.25 |
| 10Z45 | | | | |
| Initial | 44.19 | | 46.23 | |
| 26 mm | 34.4 | 22.09 | 39.87 | 14.26 |
| 28 mm | 32.4 | 26.75 | 38.59 | 17.29 |
| 30 mm | 30.9 | 30.16 | 37.39 | 19.28 |
| 10Z50 | | | | |
| Initial | 49.53 | | 51.81 | |
| 26 mm | 41 | 17.34 | 44.27 | 14.70 |
| 28 mm | 37.1 | 25.40 | 43.06 | 17.51 |
| 30 mm | 32.6 | 34.4 | 41.58 | 20.22 |
| 10Z55 | | | | |
| Initial | 55.37 | | 57.39 | |
| 26 mm | 42.4 | 23.32 | 48.97 | 14.67 |
| 28 mm | 40 | 27.58 | 47.51 | 17.22 |
| 30 mm | 36.4 | 34.17 | 45.94 | 19.95 |
| 10Z60 | | | | |
| Initial | 60.7 | | 62.91 | |
| 26 mm | 48.5 | 20.20 | 53.34 | 15.29 |
| 28 mm | 43.9 | 27.87 | 51.45 | 18.32 |
| 30 mm | 41.1 | 32.55 | 49.34 | 21.34 |

As characterized by the foregoing Table 1, each of the stents 300 demonstrate significantly less axial shrinkage in all instances, as compared to the prior known stents 200 of the same size and general dimensions. Moreover, the reduction in axial shrinkage becomes more marked as the diameter of each stent 300 increases when compared to a corresponding stent 200 having the same expansion. For example and referring to the above-listed 8Z45 stent, the prior stent 200 exhibits almost 35 percent axial shrinkage at an expanded diameter of 24 mm, while the new stent 300 exhibits one half (just under 17.5 percent) of the axial shrinkage of the prior stent 200. Similar improvements are shown in all of the above listed examples.

Figure 7A:
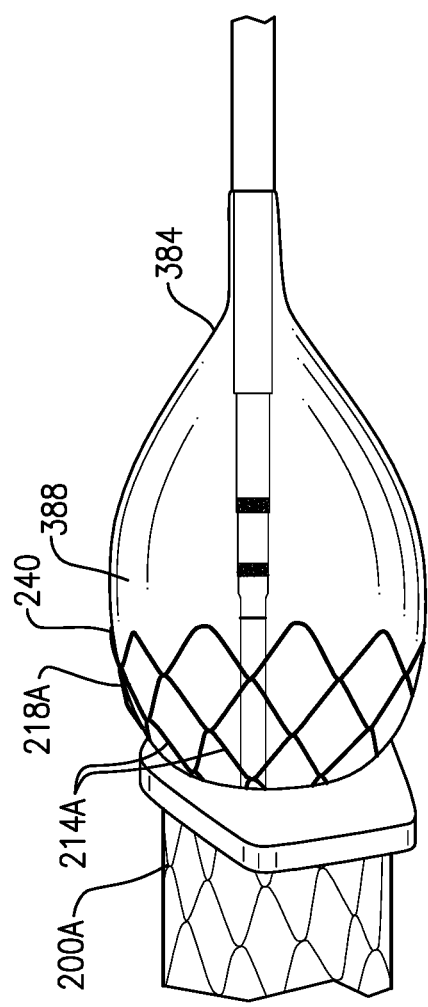
FIGS. 7(a) is a perspective view of a known intravascular stent which is radially inflated using a balloon catheter.
Figure 7B:
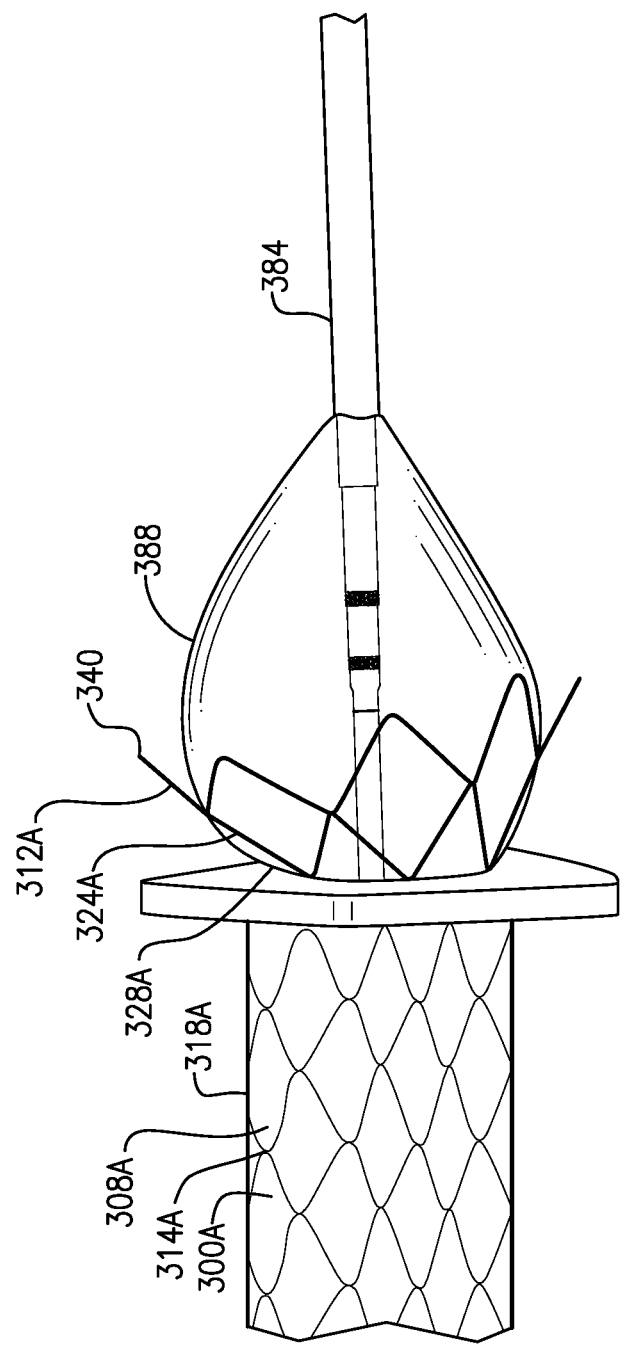
FIG. 7(b) is a perspective view of a stent made in according to aspects of the invention, shown as radially inflated using a balloon catheter and exhibiting a flaring effect at the end.

The inclusion of end portions having wire segments having longer sinusoidal bends according to the improved design creates another advantageous effect as compared to the prior know stents 200, as shown with reference to FIGS. 7(a) and 7(b). More specifically, FIG. 7(a) depicts a known stent, labeled 200A, which is made in accordance with the known design previously described according to FIGS. 3 and 4. The stent 200A is disposed in a known manner onto a balloon catheter 384 and the balloon 388 is inflated to a predetermined diameter. According to this example, each wire segment 214A of the stent 200A has a total of ten (10) formed sinusoidal bends 218A in a serpentine pattern. Following the forming of the sinusoidal bends 218A, each of the wire segments 214A are disposed over a mandrel or similar structure (not shown) to create a cylindrical configuration, with adjacent wire segments 214A being welded to one another at respective apices. In the prior stent 200A and as previously noted, all of the wire segments 214A are defined by the same initial length, as well as the same number (frequency) of sinusoidal bends 218A, each having the same length (amplitude).

By way of comparison, FIG. 7(b) depicts a stent herein labeled as 300A, which is made in accordance with the prior embodiment, see FIGS. 5 and 6. That is, the stent 300A is defined by a center portion 308A made up of a plurality of first wire segments 314A and at least one end portion 312A made up of a plurality of second wire segments 324A, each of the wire segments 314A, 324A being made from a highly malleable material that has been annealed to remove as much spring memory as possible. According to this embodiment, the stent 300A is made from an alloy of 90 percent platinum and 10 percent iridium, although other highly malleable materials can be used, such as cobalt chromium or nitinol. The first and second wire segments 314A, 324A are commonly defined by wire ribbons with the initial (unformed) length of each of the first wire segments 314A being shorter than the initial (unformed) length of each of the second wire segments 324A.

A series of sinusoidal bends 318A, 328A are formed in each of the first and second wire segments 314A, 324A in which the same number of bends are formed, but in which the amplitude (length) of the sinusoidal bends 318A, 328A are greater in the second wire segments 324A. Accordingly, the finished or formed length of the first and second wire segments 314A, 324A is the same length. The formed first and second wire segments 314A, 324A are disposed onto a mandrel or similar structure to create a cylindrical structure with adjacent wire segments being welded to one another at the apices of the formed sinusoidal bends 318A, 328A. In this example, the second wire segments 324A are provided at each of the end portions 312A (only one shown) and in which at least two of the second wire segments 324A are disposed adjacently at each end portion 312A. As shown in FIG. 7(b), the stent 300A is disposed on the balloon catheter 384 shown with the balloon 388 being inflated to the same predetermined (30 mm) diameter as stent 200A, FIG. 7(a).

Still referring to FIGS. 7(a) and 7(b) and prior to inflation, each stent 200A, 300A has an initial diameter of approximately 19 mm. Upon inflation of the balloon to the predetermined diameter, each stent 200A, 300A radially expands, wherein the terminal end 340A of the stent 300A outwardly flares relative to the inflated balloon 388. In this specifically illustrated example, the terminal end 340A of the stent 300A has a measured diameter of 36.5 mm as compared to the inflated diameter (30 mm) of the balloon 388. Comparatively, the terminal end 240A of the known stent 200A only exhibits a flared diameter of 30.92 mm relative to the inflated (30 mm) diameter of the balloon 388. This flaring effect at the terminal end 340 of the stent 300A can be desirable and has a number of advantages depending on the specific procedure. For example, and when the herein described stent is used for treatment of coarctation of the aorta, the flaring effect provides improved sealing in patients with dilated aortas on either side of the coarctation. Otherwise and when used for treatment of the right ventricular outflow tract, the flaring effect provides better stent stability without the need to over-dilate the central portion of the outflow tract. Moreover, there is a decreased risk of coronary compression regarding adjacent blood vessels due to applied pressure from the stent. There is a decreased risk of compression of adjacent blood vessels, such as the coronary arteries, as the central portion of the stent expands less than the flared ends, leaving space for the adjacent vessels to function normally. Additionally and in treating a sinus venous atrial septal defect, the flaring of the terminal end of the stent provides better stent stability without the need to over-dilate the central portion as well as decreased risk of pulmonary vein restriction. As to the noted coronary or vein restriction and in stent procedures, there is a risk in the restriction of blood flow in a vessel that is located adjacent to the area that is being stented, due to the pressure applied by the expanded stent on adjacent blood vessels (artery or vein).

Figure 8:
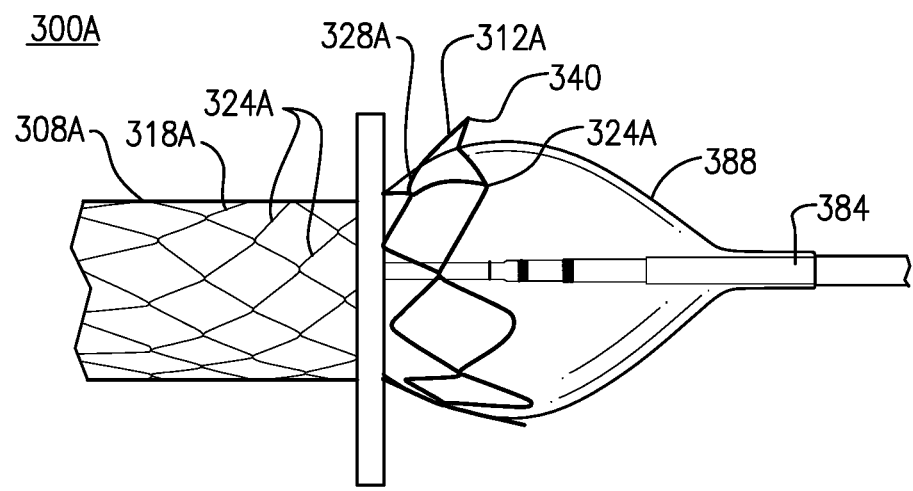
FIG. 8 is a perspective view comparing the stent of FIG. 7(b) with a stent made in accordance with other aspects of the invention.
Figure 8:
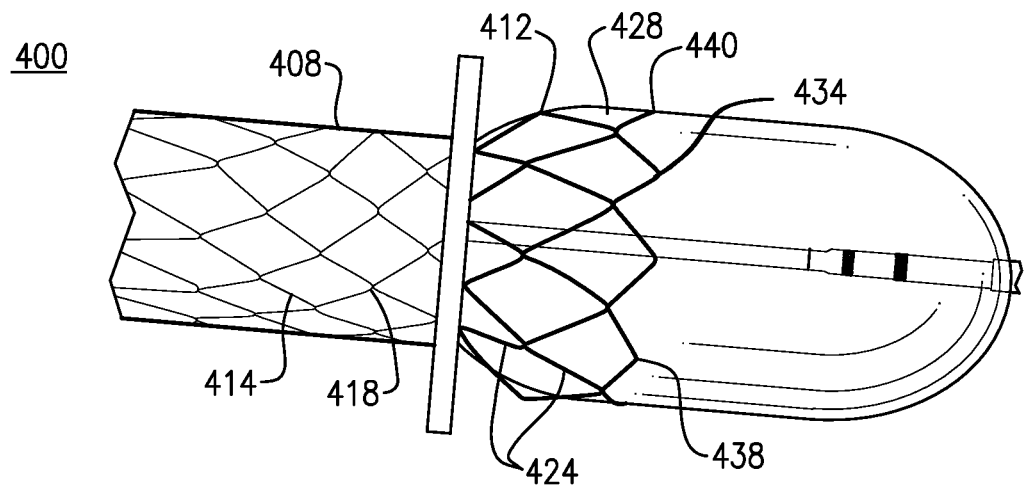

If needed, the above-noted flaring effect can also be minimized, while still minimizing axial shrinkage of the stent upon radial inflation. As shown in FIG. 8, the prior intraluminal stent 300A having the flared terminal end 340 is compared to a stent 400 made in accordance with another embodiment. The stent 400 includes a center portion 408 made up of a plurality of first wire segments 414 and end portions 412 (only one being shown) made up of a plurality of second wire segments 424. Each of the first and second wire segments 414, 424 have different unformed (initial) lengths, with the wire segments 414, 424 being made from a highly malleable material that has been annealed to remove as much spring memory as possible. Each wire segment 414, 424 is formed with a series of sinusoidal bends 418, 428 in a serpentine pattern in which the length of the sinusoidal bends 428 of the second wire segments 424 is longer than the length of the sinusoidal bends 418 of the first wire segments 414. In addition and according to this embodiment, at least one third wire segment 424 is further provided in which the third wire segment(s) 434 has an initial (unformed) length that is shorter than the initial length of each second wire segment 424, the at least one third wire segment 434 also having a formed series of sinusoidal bends 438 which are equal in number to that of the first and second wire segments 414, 424, but in which the length (amplitude) of the sinusoidal bends 438 of the third wire segment(s) 434 is shorter than that of the second wire segments 424. In at least one version, the length of the third wire segment(s) 434, as well as the length of the sinusoidal bends 438 can be substantially equal to the length of the sinusoidal bends 418 of the first wire segments 414.

According to a preferred embodiment, the first, second and third wire segments 414, 424, 434 are disposed onto a cylindrical mandrel (not shown) with the first wire segments 414 being provided at a center portion 404, the second wire segments 424 being disposed at end portions 412 (only one being shown) of the stent 400 and the at least one third wire segment 434 being disposed at one or both terminal ends 440 (only one shown) of the stent 400. As in the prior embodiment, respective apices of the sinusoidal bends 418, 428, 438 of the adjacently disposed wire segments 414, 424, 434 are welded to one another.

As shown, each of the stents 300A and 400 are disposed onto the balloon catheter 384 and with a portion of the stents 300A, 400 being disposed onto the inflatable balloon 388. Upon inflation to a predetermined diameter, the terminal end 340 of the stent 300A outwardly flares, as previously described with regard to FIG. 7(b). However, the stent 400 having the third wire segment 434 does not result in a pronounced flaring effect, but in which minimized axial shrinkage is still realized due to the end portions having the at least two second wire segments 424 having the longer sinusoidal bends 428. It will be understood that other suitable configurations can be provided.

PARTS LIST FOR FIGS. 1-8

100 intraluminal stent
104 plurality of elongate members
108 intersecting points
110 balloon catheter
114 inflatable balloon
120 blood vessel
124 occluded portion, blood vessel 126 interior wall, blood vessel
L1 initial axial length, stent
L2 expanded axial length, stent
200 intraluminal stent
200A intraluminal stent
214 plurality of wire segments (ribbons/strands)
214A plurality of wire segments(ribbons/strands)
218 sinusoidal bends
218A sinusoidal bends
224 connection (weld) points
240 terminal end
300 intraluminal stent
300A intraluminal stent
308 center section, stent
308A center portion
312 end section, stent
314 plurality of first wire segments
314A plurality of first wire segments
318 first sinusoidal bends
318A first sinusoidal bends
324 plurality of second wire segments
324A second sinusoidal bends
328 second sinusoidal bends
332 connection (weld) points
340 terminal end, stent
384 balloon catheter
388 balloon
400 intraluminal stent
408 center portion
412 end portion(s)
414 plurality of first wire segments
418 first sinusoidal bends
424 plurality of second wire segments
428 second sinusoidal bends
434 third wire segment
438 third sinusoidal bends
440 terminal end It should be readily apparent from the foregoing description that there are several modifications and variations that can be made to the exemplary embodiments described herein. Each of these modifications and variations are intended to be within the scope of the invention, and as set forth according to the following claims.

The invention claimed is:

1. An intraluminal stent for deployment within a blood vessel in order to keep the blood vessel open, the intraluminal stent comprising:
a cylindrically shaped structure including a center portion made up of a plurality of first wire segments, each of the first wire segments having an initial total length; and
at least one end portion being made up a plurality of second wire segments, each of the second wire segments having an initial total length that is longer than the initial total length of each of the first wire segments, wherein each of the first and second wire segments are subsequently formed with a series of sinusoidal bends in which the length (amplitude) of each of the sinusoidal bends formed in the second wire segments is larger than the length of each of the sinusoidal bends formed in the first wire segments but in which each of the first and second wire segments have the same number of sinusoidal bends formed over their total length in which the series of sinusoidal bends is staggered between adjacent wire segments, each of the sinusoidal bends having a peak and a valley in which the wire segments are attached to each another by welding each of the peaks of a wire segment with the valley of an adjacent wire segment over the length of each of the wire segments, and in which the first and second wire segments are each made from a malleable material that has shape memory removed such that when disposed onto and radially expanded by a balloon catheter, the stent exhibits limited axial shrinkage within a blood vessel within which the stent has been implanted and in which each of the center portion and at least one end portion of the stent substantially maintains its cylindrical shape following radial expansion of the stent by the balloon catheter with resulting axial contact of the center portion and at least one end portion of the stent with an inner circumferential wall of the blood vessel for maintaining an open condition of the blood vessel.

2. The stent according to claim 1, wherein at least two second wire segments are disposed at opposing end portions of the stent and three first wire segments form the center portion of the stent.

3. The stent according to claim 1, wherein only one end portion of the stent is made up of two or more second wire segments.

4. The stent according to claim 1, wherein the at least one end portion of the stent having the at least two second wire segments is configured to outwardly flare relative to the center portion of the stent upon radial expansion.

5. The stent according to claim 2, further comprising a third wire segment disposed at a terminal end of the stent, the third wire segment having an initial total length that is shorter than the total length of each of the second wire segments, the third wire segment having a series of sinusoidal bends formed in a serpentine pattern in which each of the respective apices of the series of sinusoidal bends are welded to an adjacent second wire segment.

6. The stent according to claim 5, in which an initial length and the amplitude of each of the sinusoidal bends formed in the third wire segment is substantially equal to the initial length and amplitude of each of the sinusoidal bends formed in the first wire segment.

7. A stent implantation system comprising:
an inflatable balloon catheter; and
an intraluminal stent according to claim 1.

8. The stent implantation system according to claim 7, wherein at least two second wire segments are attached to each of opposing end portions of the stent.

9. The stent implantation system according to claim 8, wherein two or more second wire segments are attached to only one end portion of the stent.

10. The stent implantation system according to claim 8, further comprising a third wire segment disposed at a terminal end of the stent, the third wire segment having an initial total length and a series of formed sinusoidal bends disposed over the total length wherein the initial length and amplitude of the formed sinusoidal bends of the third wire segment are shorter than the initial length and the amplitude, respectively, of the sinusoidal bends of the second wire segments, the third wire segment being welded at each of the respective apices of the sinusoidal bends to an adjacent second wire segment.

11. The stent implantation system according to claim 7, wherein at least one end portion of the stent having the at least two second wire segments is configured to outwardly flare upon radial expansion by the balloon catheter.

12. An intraluminal stent for deployment within a blood vessel comprising:

a cylindrically shaped structure including a center portion made up of a plurality of first wire segments, each of the first wire segments having an initial total length;

at least one end portion being made up a plurality of second wire segments, each of the second wire segments having an initial total length that is longer than the initial total length of each of the first wire segments, wherein each of the first and second wire segments are subsequently formed with a series of sinusoidal bends in which the length (amplitude) of each of the sinusoidal bends formed in the second wire segments is larger than the length of each of the sinusoidal bends formed in the first wire segments but in which each of the first and second wire segments have the same number of sinusoidal bends formed over their total length in which the series of sinusoidal bends is staggered between adjacent wire segments, each of the sinusoidal bends having a peak and a valley in which the wire segments are attached to each another by welding each of the peaks of a wire segment with the valley of an adjacent wire segment over the length of each of the wire segments, and in which the first and second wire segments are each made from a malleable material that has shape memory removed such that when disposed onto and radially expanded by a balloon catheter, the stent exhibits limited axial shrinkage within a blood vessel within which the stent has been implanted, and a third wire segment disposed at a terminal end of the stent, the third wire segment having an initial total length that is shorter than the total length of each of the second wire segments, the third wire segment having a series of sinusoidal bends formed in a serpentine pattern in which each of the respective apices of the series of sinusoidal bends are welded to an adjacent second wire segment, in which an initial length and the amplitude of each of the sinusoidal bends formed in the third wire segment is substantially equal to the initial length and amplitude of each of the sinusoidal bends formed in the first wire segment.

\* \* \* \* \*